United States Patent [19]

Hässig et al.

[11] Patent Number: 5,274,100
[45] Date of Patent: Dec. 28, 1993

[54] PROCESS FOR THE PREPARATION OF (3-FLUOROPYRIDIN-2-YLOXY)PHENOXY-PROPIONIC ACIDS

[75] Inventors: Robert Hässig, Gipf-Oberfrick; Urs Siegrist, Eiken, both of Switzerland

[73] Assignee: Ciba-Geigy Corporation, Ardsley, N.Y.

[21] Appl. No.: 974,778

[22] Filed: Nov. 12, 1992

Related U.S. Application Data

[63] Continuation-in-part of Ser. No. 777,862, Oct. 16, 1991, abandoned.

[30] Foreign Application Priority Data

Oct. 23, 1990 [CH] Switzerland ............ 3379/90

[51] Int. Cl.⁵ .................................. C07D 213/64
[52] U.S. Cl. .................................. 546/302
[58] Field of Search ........................ 546/302

[56] References Cited

U.S. PATENT DOCUMENTS

| | | | |
|---|---|---|---|
| 4,505,743 | 3/1985 | Schurter et al. | 71/94 |
| 4,640,703 | 2/1987 | Böhner et al. | 71/92 |
| 4,759,796 | 7/1988 | Böhner et al. | 71/94 |
| 4,831,148 | 5/1989 | Schurter et al. | 546/345 |

FOREIGN PATENT DOCUMENTS

| | | | |
|---|---|---|---|
| 0248968 | 12/1987 | European Pat. Off. | 546/345 |
| 0305593 | 3/1989 | European Pat. Off. | 546/346 |

OTHER PUBLICATIONS

Ferm et al., J. American Chem. Soc., 72, p. 4809, (1950).

Primary Examiner—C. Warren Ivy
Assistant Examiner—Zinna N. Davis
Attorney, Agent, or Firm—Marla J. Mathias; Kevin T. Mansfield

[57] ABSTRACT

(3-Fluoropyridin-2-yloxy)phenoxypropionic acids of formula I

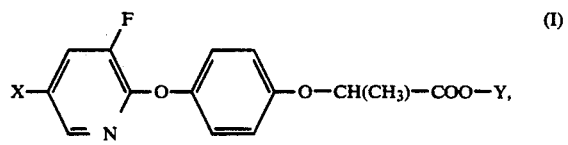

wherein X is hydrogen, fluoro, chloro, bromo or trifluoromethyl and Y is hydrogen, sodium or potassium, are prepared by reacting a compound of formula II

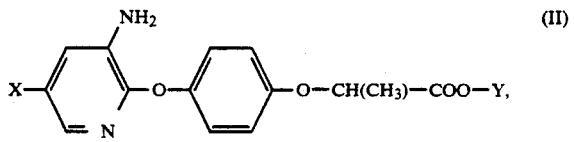

wherein X and Y are as defined for formula I, in an anhydrous mixture of hydrogen fluoride, dimethylsulfoxide and a diazotising agent under normal pressure, and converting the diazonium fluoride so produced by thermal decomposition into the (3-fluoropyridin-2-yloxy)phenoxypropionic acid of formula I.

7 Claims, No Drawings

PROCESS FOR THE PREPARATION OF (3-FLUOROPYRIDIN-2-YLOXY)PHENOXYPROPIONIC ACIDS

This is a continuation-in-part of application Ser. No. 777,862 filed Oct. 16, 1991, now abandoned.

The present invention relates to an improved process for the preparation of (3-fluoropyridin-2-yloxy)phenoxypropionic acids of formula I

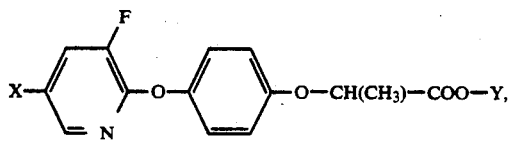

wherein X is hydrogen, fluoro, chloro, bromo or trifluoromethyl and Y is hydrogen, sodium or potassium.

The (3-fluoropyridin-2-yloxy)phenoxypropionic acids and salts of formula I have herbicidal properties. Furthermore, they are useful intermediates for the synthesis of the herbicidally active (3-fluoropyridin-2-yloxy)phenoxypropionates disclosed, inter alia, in published European patent application EP-A-0 248 968 and in U.S. Pat. No. 4,505,743. The fluorination of [4-(3-amino-5-chloropyridyl-2-oxy)-phenoxy]-propionic acid methyl ester using hydrofluoboric acid is described in U.S. Pat. No. 4,505,743. Disadvantages of this process include a low yield and the necessity to isolate the diazonium tetrafluoroborate prior to thermal decomposition.

The fluorination of (3-aminopyridin-2-yloxy)phenoxy derivatives is illustrated as part of a synthesis of 2-pyridinyloxy-phenoxy-propiocyanamides in the examples in U.S. Pat. No. 4,640,703 using pure hydrogen fluoride combined with diazonium intermediate-formation at elevated pressure. Weaknesses of this process include the formation of side products and the inconvenience of working at elevated pressures.

U.S. Pat. No. 4,831,148 describes the fluorination of simple pyridine derivatives via a diazonium intermediate using, for the 3-position, a mixture of hydrogen fluoride and an inert solvent under normal pressure at the decomposition temperature of the diazonium intermediate. The problem of selectivity, however, does not arise with such simple molecules.

In the practice of the fluorination of (3-aminopyridin-2-yloxy)phenoxy propionic acid derivatives, the main side products are aza-9-oxofluorene derivatives of formula V

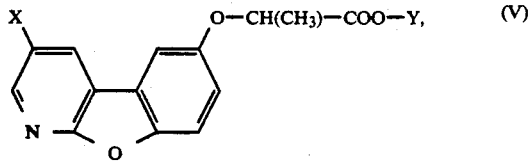

wherein X and Y are as defined for formula I above. A process for preparing 1-aza-9-oxafluorenes is described in British patent specification 1 300 928 in which, for example, 3-amino-2-phenoxypyridine is cyclised in the presence of copper powder and acidified aqueous sodium nitrite to give 1-aza-9-oxafluorene.

The side products of formula V are produced in considerable amounts in prior art processes using (3-aminopyridin-2-yloxy)phenoxy propionic acid which causes considerable inconvenience when produced on an industrial scale. It is therefore desirable to reduce costly purification time by following a process in which negligible or only very small amounts of side product are produced.

It is the object of this invention to provide an improved process which allows (3-fluoropyridin-2-yloxy)-phenoxypropionic acids to be prepared in a simple manner, in good yield and high purity, starting from readily accessible starting materials, and which is particularly suitable as an industrial production process.

Surprisingly, it has now been found that the formation of side products can be substantially suppressed when (3-aminopyridin-2-yloxy)phenoxy propionic acids are fluorinated via their diazonium salts in an anhydrous medium containing dimethylsulfoxide.

The object of the present invention is to prepare (3-fluoropyridin-2-yloxy)phenoxypropionic acids of formula I in good yield and high purity by reacting a compound of formula II

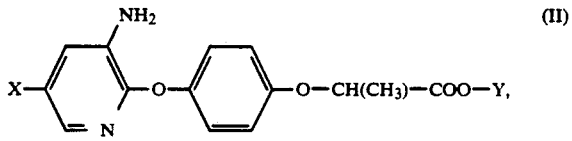

wherein X and Y are as defined for formula I, with a diazotising agent and converting the diazonium fluoride so produced by thermal decomposition into the (3-fluoropyridin-2-yloxy)phenoxypropionic acid of formula I or the sodium or potassium salt thereof, the improvement in which process comprises carrying out the reaction in an anhydrous mixture of hydrogen fluoride and dimethylsulfoxide under normal pressure.

The final products of the process of this invention are known. The starting materials of formula II can be obtained by reduction methods from the corresponding nitro compounds of formula III

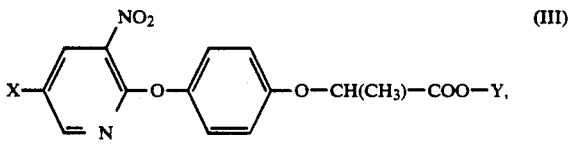

wherein X and Y are as defined for formula I. All standard methods described in the literature can be used for reducing the nitro compounds of formula III to the amino compounds of formula II. The reduction can typically be carried out with advantage in aqueous medium in the presence of iron, tin or zinc and hydrochloric acid. Other suitable methods are reduction processes using complex hydrides such as lithium aluminium hydride, or catalytic reduction with hydrogen using platinium, palladium or nickel catalysts.

The compounds of formula III can be prepared by methods which are known per se, typically by reacting the corresponding 2-chloro-3-nitropyridines with 2-(4-hydroxy)phenoxypropionic acid in the presence of a base. Such processes are described, for example, in EP-A-0 248 968. The 2-chloro-3-nitropyridines required for the preparation of the compounds of formula III, as well as the 2-(4-hydroxy)phenoxypropionic acid, are known or can be obtained by methods which are known to the skilled person.

The diazotisation can be carried out in the temperature range from −20° to +25° C., preferably from −10° to +10° C.

Preferred diazotising agents are sodium nitrite, potassium nitrite, N₂O₃, NOF, NOCl, isoamyl nitrite or tert-butyl nitrite. A particularly preferred diazotising agent is sodium nitrite.

The thermal decomposition of the diazonium fluoride of formula IV

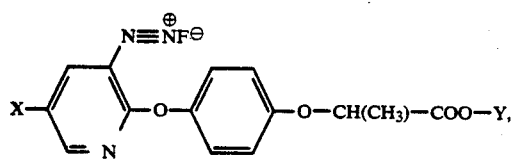

wherein X and Y are as defined for formula I, is normally carried out in the temperature range from 15° to 100° C., preferably from 30° to 60° C. A particularly preferred temperature range is from 45° to 60° C.

The improved process according to the invention thus comprises preferably reacting 4-(5-chloro-3-aminopyridin-2-yloxy)phenoxypropionic acid in an anhydrous mixture of hydrogen fluoride and dimethylsulfoxide at a temperature in the range from 45° to 60° C. with sodium nitrite under atmospheric pressure.

The process of this invention can be carried out in two steps as well as in one step. In the two-step variant of the process, the diazonium fluoride is prepared in the first step and thermally decomposed in the second step. In the particularly preferred single step variant of the process, the diazotisation is carried out at the decomposition temperature of the diazonium fluoride which forms in situ and is converted direct into the compound of formula I.

By means of the process of this invention it is possible to prepare the 4-(5-chloro-3-aminopyridin-2-yloxy)-phenoxypropionic acids of formula I from readily accessible starting materials in a simple manner, in good yield and in high selectivity and purity. Another advantage of the process of this invention is that the unstable and explosive diazonium salt intermediates do not have to be isolated from the reaction medium. In addition, no environmentally undesirable boron trifluoride wastes form.

Due to the surprisingly favourable selectivity afforded by the process according to the invention, the compound of formula I is formed in very high purity. It is furthermore surprising that the competing reaction described in GB patent specification 1 300 928 is almost completely suppressed, so that the side products of formula V are formed in very small quantities compared with the amounts formed when using reaction processes described in the prior art.

The following Examples illustrate the process of the invention in more detail.

WORKING EXAMPLES:

A) Preparation of the starting materials

EXAMPLE A1

Preparation of 5-chloro-2-aminopyridine

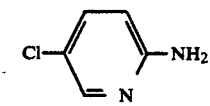

941 g of 2-aminopyridine are added at a temperature of 10° C. over 30 minutes to 4 l of concentrated hydrochloric acid. Then 745 g of chlorine gas is introduced over 8½ hours at a temperature of 10° C. The reaction mixture is stirred for 18 hours and then neutralised at a temperature of 10°-20° C. with 5.9 l of concentrated sodium hydroxide solution to a pH of 7-8. The precipitated crude product is isolated by filtration, washed with ice-water and subsequently dried at 40° C. For purification, the crude product is suspended in water and then collected by filtration. The product is suspended in petroleum ether, isolated by filtration and dried, giving 991 g (77.1% of theory) of 5-chloro-2-aminopyridine with a melting point of 128°-130° C. in 95% purity.

EXAMPLE A2

Preparation of 5-chloro-2-hydroxy-3-nitropyridine

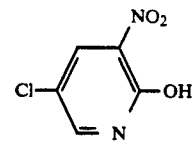

321 g of 5-chloro-2-aminopyridine are added dropwise to 1.25 l of concentrated sulfuric acid. The reaction mixture is then stirred until the educt has completely dissolved. Then 172.5 g of sodium nitrite, dissolved in 240 ml of water, are added at a temperature of 40°-45° C. and the reaction mixture is stirred for 15 minutes. Subsequently 125 ml of 100% nitric acid are added dropwise at 50° C. over 40 minutes. The reaction mixture is kept for 1 hour at 55° C. and then poured onto 5 kg of ice-water. The product in the form of a yellow precipitate is isolated by filtration, washed copiously with water and subsequently dried at 60° C., giving 351 g of 5-chloro-2-hydroxy-3-nitropyridine (80.5% of theory) with a melting point of 229°-231° C.

EXAMPLE A3

Preparation of 2,5-dichloro-3-nitropyridine

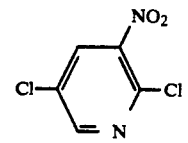

75 g of phosgene are introduced at a temperature of 85°-95° C. over 1 hour into a mixture of 87.5 g of 5-chloro-2-hydroxy-3-nitropyridine in 500 ml of toluene and 3 ml of N,N-dimethylformamide. The reaction mixture is kept for 2 hours under reflux at 85°-95° C.

and then allowed to cool to room temperature over a period of 18 hours. The reaction mixture is washed 3 times with water and the organic phase is dried over sodium sulfate and thereafter concentrated by evaporation. The crude product, obtained in the form of a brown oil, is crystallised from 200 ml of n-hexane, giving 67.5 g of 2,5-dichloro-3-nitropyridine (70% of theory) with a melting point of 38°-39° C.

EXAMPLE A4

Preparation of 2-(4-(5-chloro-3-nitropyridin-2-yloxy)phenoxy)propionic acid

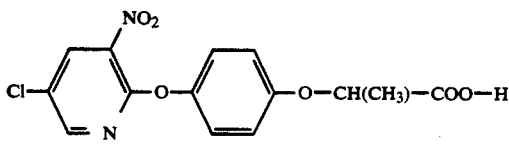

56.1 g of a 50% aqueous solution of potassium hydroxide are added dropwise at room temperature to a suspension of 91 g of water and 92.3 g of 2-(4-hydroxy)-phenoxypropionic acid. After the removal of water by distillation, the potassium salt so obtained is dissolved in 390 g of N,N-dimethylformamide, and then 108.1 g of 2,5-dichloro-3-nitropyridine in 95 g of N,N-dimethylformamide are added dropwise at 85° C. The reaction mixture is stirred for 90 minutes at 85° C., then poured into water and 100 ml of concentrated hydrochloric acid are added dropwise. The oily crude product is extracted with toluene. The organic phase is concentrated by evaporation, giving 188 g (92% of theory) of 2-(4-(5-chloro-3-nitropyridin-2-yloxy)phenoxy)propionic acid.

EXAMPLE A5

Preparation of 2-(4-(5-chloro-3-aminopyridin-2-yloxy)phenoxy)propionic acid

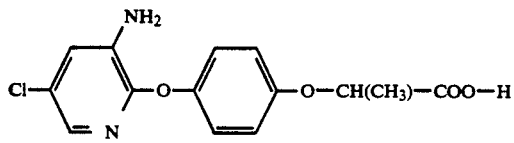

20 g of Raney nickel catalyst are added to a solution of 196 g of 2-(4-(5-chloro-3-nitropyridin-2-yloxy)-phenoxy)propionic acid in 615 g of dioxane, and hydrogenation is subsequently carried out at 20°-22° C. under normal pressure. After separating the catalyst the solvent is removed, giving 98 g of 2-(4-(5-chloro-3-aminopyridin-2-yloxy)phenoxy)propionic acid as crude product (55% of theory) which has a melting point of 152°-154° C. and can be recrystallised from toluene.

B) Preparation of the Final Products

EXAMPLE B1

Preparation of 2-(4-(5-chloro-3-fluoropyridin-2-yloxy)phenoxy)propionic acid under normal pressure in DMSO (invention)

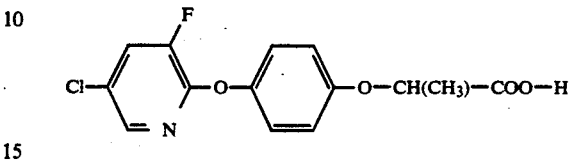

A polyethylene reactor is charged with 150 g of hydrogen fluoride and cooled to $-78°$ C. Then a solution of 31.2 g of 2-(4-(5-chloro-3-aminopyridin-2-yloxy)-phenoxy)propionic acid in 82.5 g of dimethylsulfoxide is added dropwise over 1 hour at a temperature of $-20°$ to $+10°$ C. The reaction mixture is slowly heated to 50° C. and 7.4 g of sodium nitrite are then added in portions at a maximum temperature of 60° C. over a period of 90 minutes. The reaction mixture is thereafter cooled to room temperature and, after addition of ethyl acetate, is stirred into ice and then neutralised with concentrated ammonia to pH 3–4. After repeated extraction with ethyl acetate, the organic phases are extracted with water until the pH is about 7. The combined organic phases are dried over sodium sulfate and the solvent is removed, giving 30 g of the title compound with a melting point of 90° to 92° C. HPLC-analysis shows the following composition:

88% 2-(4-(5-chloro-3-fluoropyridin-2-yloxy)phenoxy)-propionic acid,

2% of the main side product of formula Va

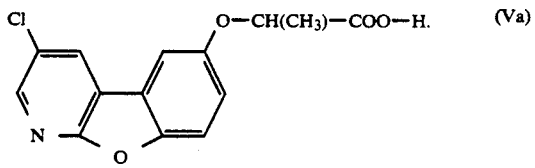

The product can be recrystallised from methanol/-water or toluene.

EXAMPLE B2

Preparation of 2-(4-(5-chloro-3-fluoropyridin-2-yloxy)phenoxy)propionic acid without DMSO (as exemplified in U.S. Pat. No. 4,640,703)

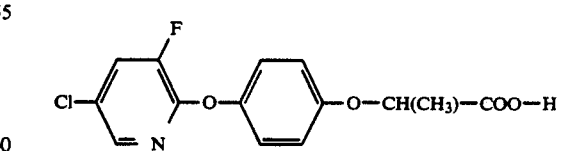

A polyethylene reactor is charged with 75 g of hydrogen fluoride and cooled to $-78°$ C. Then 7.4 g of sodium nitrite are added in portions at a temperature of $-10°$ to 0° C. The solution is run into an evacuated, pressure-resistant autoclave. The pressure is then increased to 3 MPa by introducing nitrogen and the temperature is kept at 0° C.

A pressure-resistant autoclave is charged with 31.2 g of 2-(4-(5-chloro-3-aminopyridin-2-yloxy)phenoxy)propionic acid, evacuated and cooled to −78° C. Then 50 g of hydrogen fluoride are added and the reaction mixture is heated to 50° C. At this temperature a solution of sodium nitrite and hydrogen fluoride in liquid form, which is under a pressure of 3 MPa, is run in over 1 hour. The reaction mixture is stirred for 1 hour at 50° C. and under a pressure of 2.4 MPa, then cooled to room temperature. The pressure in the autoclave is reduced to normal pressure, excess hydrogen fluoride is removed with suction and the oily residue is dissolved in ethyl acetate. The solution is neutralised with ammonia to pH 3. The organic phase is separated and the aqueous phase is extracted 3 times with ethyl acetate. The combined organic phases are extracted with water until the pH is about 7. The ethyl acetate solution is dried over sodium sulfate and the solvent is removed, giving 26.5 g of the title compound with a melting point of 90° to 92° C. HPLC-analysis shows the following composition:

77% 2-(4-(5-chloro-3-fluoropyridin-2-yloxy)phenoxy)-propionic acid, 13.6% of the main side product of formula Va.

The product can be recrystallised from methanol/-water or toluene.

What is claimed is:

1. A process for the preparation of a (3-fluoropyridin-2-yloxy)phenoxypropionic acid of formula I

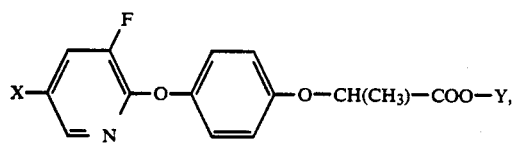

wherein X is hydrogen, fluoro, chloro, bromo or trifluoromethyl and Y is hydrogen, sodium or potassium, by reacting a compound of formula II

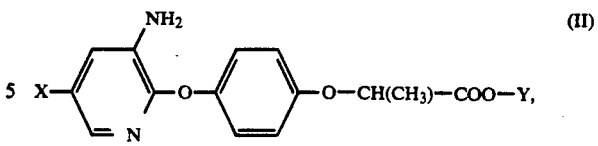

wherein X and Y are as defined for formula I, with a diazotising agent and converting the diazonium fluoride so produced by thermal decomposition into the (3-fluoropyridin-2-yloxy)phenoxypropionic acid of formula I or the sodium or potassium salt thereof, the improvement in which process comprises carrying out the reaction in an anhydrous mixture of hydrogen fluoride and dimethylsulfoxide under normal pressure.

2. A process according to claim 1, wherein the thermal decomposition is carried out in the temperature range from 30° to 60° C.

3. A process according to claim 1, wherein the thermal decomposition is carried out in the temperature range from 45° to 60° C.

4. A process according to claim 1, wherein the diazotising agent is selected from the group consisting of sodium nitrite, potassium nitrite, $N_2O_3$, NOF, NOCl, isoamyl nitrite and tert-butyl nitrite.

5. A process according to claim 1, wherein the diazotising agent is sodium nitrite.

6. A process according to claim 1, which comprises adding the diazotising agent to an anhydrous mixture of hydrogen fluoride, DMSO and the compound of formula II.

7. A process according to claim 1, which comprises reacting an anhydrous mixture of hydrogen fluoride and 4-(5-chloro-3-aminopyridin-2-yloxy)phenoxypropionic acid, in the presence of dimethylsulfoxide under normal pressure and in the temperature range from 45° to 60° C., with sodium nitrite.